US005728527A

United States Patent [19]
Singer et al.

[11] Patent Number: 5,728,527
[45] Date of Patent: Mar. 17, 1998

[54] DETECTION OF HYBRIDIZED OLIGONOCLEOTIDE PROBES IN LIVING CELLS

[75] Inventors: Robert H. Singer, Shrewsbury; Joan C. Politz, Holden; Krishan Taneja, Northboro, all of Mass.

[73] Assignee: University of Massachusetts Medical Center, Worcester, Mass.

[21] Appl. No.: 485,314

[22] Filed: Jun. 7, 1995

Related U.S. Application Data

[63] Continuation-in-part of Ser. No. 94,510, Jul. 20, 1993, abandoned.
[51] Int. Cl.$^6$ .............................. C12Q 1/68; C12Q 1/70; A61K 48/00; C07H 21/04
[52] U.S. Cl. .............................. 435/6; 435/5; 435/91.2; 514/44; 536/24.5; 536/24.3; 536/24.32; 536/24.33
[58] Field of Search ....................... 435/6, 91.2, 5; 514/44; 536/24.5, 24.3–24.33

[56] References Cited

U.S. PATENT DOCUMENTS

| | | | |
|---|---|---|---|
| 5,225,326 | 7/1993 | Bresser et al. | 435/6 |
| 5,236,844 | 8/1993 | Basset et al. | 435/320.1 |

FOREIGN PATENT DOCUMENTS

| | | |
|---|---|---|
| 0070685A2 | 1/1983 | European Pat. Off. |
| 0229943A2 | 7/1987 | European Pat. Off. |
| WO 90/10715 | 9/1990 | WIPO |
| WO 93/05177 | 3/1993 | WIPO |
| WO 93/24652 | 12/1993 | WIPO |

OTHER PUBLICATIONS

Politz, J.C. et al., "Hybridization of Poly (dT) Oligonucleotides to Poly(A) RNA in Living Cells", *Mol. Biol. Cell 5S*: 337a (1994).
Gura, *Science* 270: 575–577, 1995.
James, *Antiviral Chemistry and Chemotherapy* 2: 191–214, 1991.
Cardullo, R.A., et al., "Detection of Nucleic Acid Hybridization by Nonradiative Fluorescence Resonance Energy Transfer", *Proc. Natl. Acad. Sci. USA* 85: 8790–8794 (1988).
Marshall, W.S., et al., "Inhibition of Human Immunodeficiency Virus Activity by Phosphorodithioate Oligodeoxycytidine", *Proc. Natl. Acad. Sci. USA* 89: 6265–6269 (1992).
Jaroszewski, J.W., et al., "Cellular Uptake of Antisense Oligonucleotides", *Advanced Drug Delivery Reviews* 6: 235–250 (1991).
Shoji, Y., et al., "Mechanism of Cellular Uptake of Modified Oligodeoxynucleotides Containing Methylphosphonate Linkages", *Nuc. Acids Res.* 19: 5543–5550.
Agrawal, S., et al., "Cellular Uptake and Anti–HIV Activity of Oligonucleotides and Their Analogs", *Gene Regulation: Biology of Antisense RNA and DNA* Erickson and Izant (Eds) Raven Press, Ltd., New York, pp. 273–283 (1992).
Marti, G., et al., "Oligodeoxyribonucleotide Phosphorothioate Fluxes and Localization in Hematopoietic Cells", *Antisense Research and Development* 2: 27–39 (1992).

Stein, C.A., et al., "Phosphorothioate and Normal Oligodeoxyribonucleotides with 5'–linked Acridine: Characterization and Preliminary Kinetics of Cellular Uptake", *Gene* 72: 333–341 (1988).
Uhlmann, E. and Peyman, A., "Antisense Oligonucleotides: A New Therapeutic Principle", *Chemical Reviews* 90(4): 543–584 (1990).
Miller, P.S., et al., "Biochemical and Biological Effects of Nonionic Nucleic Acid Methylphosphonates", *Biochemistry* 20(7): 1874–1880 (1981).
Bennett, C.F., et al., "Cationic Lipids Enhance Cellular Uptake and Activity of Phosphorothioate Antisense Oligonucleotides", *Molecular Pharmacology* 41(6): 1023–1033 (1992).
Zon, G., "Oligonucleotide Analogues as Potential Chemothrapeutic Agents", *Pharmaceutical Research* 5(9): 539–549 (1988).
Goodchild, J., "Conjugates of Oligonucleotides and Modified Oligonucleotides: A Review of their Synthesis and Properties", *Bioconjugate Chemistry* 1(3): 165–187 (1990).
Vlassov, V.V., et al., "Transport of oligonucleotides across natural and model membranes", *Biochimica et Biophysica Acta* 1197:95–108 (1994).
Zamecnik, P., et al., "Electron micrographic studies of transport of oligodeoxynucleotides across eukaryotic cell membranes", *Proc. Natl. Acad. Sci. USA* 91: 3156–3160 (1994).
Kislauskis, E.H., et al., "Isoform–specific 3'–untranslated Sequences Sort α–cardiac and β–cytoplasmic Actin Messenger RNAs to Different Cytoplasmic Compartments", *J. Cell Biology* 123(1): 165–172 (1993).
Bassell, G.J., et al., "Signal mRNAs Visualized by Ultrastructural In Situ Hybridization Are Principally Localized at Actin Filament Intersections in Fibroblasts", *J. Cell Biology* 126(4): 863–876 (1994).
Eberwine, J., et al., "Complementary DNA Synthesis in Situ: Methods and Applications", *Methods in Enzymology* 216: 80–100 (1992).
Mogensen, J., et al., "Nonradioactive, Sequence–Specific Detection of RNA in Situ by Primed in Situ Labeling (PRINS)", *Experimental Cell Research* 196: 92–98 (1991).
Feldherr, C.M. and Akin, D., "Role of Nuclear Trafficking in Regulating Cellular Activity", *International Review of Cytology* 151: 183–228 (1994).
Wintersberger, U., "Ribonucleases H of Retroviral and Cellular Origin", *Pharmac. Ther.* 48: 259–280 (1990).
Sachs, A., "The role of poly(A) in the translation and stability of mRNA", *Current Opinion in Cell Biology* 2: 1092–1098 (1990).

*Primary Examiner*—Stephanie W. Zitomer
*Assistant Examiner*—Dianne Rees
*Attorney, Agent, or Firm*—Hamilton, Brook, Smith & Reynolds, P.C.

[57] ABSTRACT

A method of nucleic acid hybridization in living cells is described, which is useful for detecting, quantitating and locating a specific nucleic acid in a cell or tissue, for selecting cells based on the expression or presence of a specific nucleic acid, and for monitoring the amount and location of a specific nucleic acid over time or under various inducing or inhibiting conditions.

28 Claims, 9 Drawing Sheets

DETECTION OF HYBRIDIZED OLIGONOCLEOTIDE PROBES IN LIVING CELLS

RELATED APPLICATION

This application is a continuation-in-part of U.S. Ser. No. 08/094,510, filed Jul. 20, 1993 now abandoned, which is incorporated herein by reference in its entirety.

DESCRIPTION

Government Support

This work was supported by Grant No. HB-67022 and HD-18066 from the National Institutes of Health. The U.S. Government has certain rights to this invention.

Background

In situ hybridization is a useful method for detecting specific nucleic acid sequences in a tissue or individual cell. It has been used to localize specific sequences on chromosomes, to localize vital or cellular mRNAs in cultured cells and tissue sections, and to determine the expression of genes during embryonic and larval (e.g. Drosophila) development (Ausubel et al., eds., *Current Protocols in Molecular Biology*, Greene Publishing Associates and Wiley-Interscience, New York, 1988, Vol. 2, pp. 14.3.11–14.3.12). In this method, the tissue is fixed and sectioned before applying the hybridization probe. The tissue preparation methods commonly used are cryosectioning, paraformaldehyde fixation and paraffin wax embedding, and plastic sectioning (Ausubel et al., eds., *Current Protocols in Molecular Biology*, Greene Publishing Associates and Wiley-Interscience, New York, 1988, Vol. 2, pp. 14.1.7–14.1.8, pp. 14.2.6–14.2.8, and pp. 14.3.11–14.3.13). These techniques are intended to preserve cellular morphology while leaving the cellular content and location of nucleic acids intact. However, they kill the cells, with the result that hybridization is actually performed on dead cells. Fixatives penetrate the cells slowly, and it is possible that, during fixation, the nucleic acids rearrange in an artifactual manner. These artifacts may involve such processes as diffusion, degradation, disassembly, polymerization or disassociation. A method allowing hybridization in vivo (i.e. in living cells) would be advantageous.

Influx and efflux of oligonucleotide phosphorothioates in hematopoietic cells for the purpose of future usefulness in antisense research has been described (Marti et al., *Antisense Research and Development* 2:27–29, 1992).

SUMMARY OF THE INVENTION

This invention relates to a method of nucleic acid hybridization performed in vivo, that is on living cells. According to this method, modified and unmodified oligonucleotide probes are taken up rapidly and quantitatively by living cells, hybridize to complementary nucleic acids in the cells, and excess probes are washed from the cells, permitting detection and quantitation of specific hybridization within the living cells. The probes are single-stranded oligonucleotides that can be used in unmodified form or they can be modified to increase their ability to penetrate through hydrophobic cellular membranes. The probes are also labelled with a detectable marker, such as a fluorochrome. Although not wishing to be bound by theory, it is believed that such modified, unmodified and labelled oligonucleotides appear to enter living cells by passive diffusion.

As described herein, this hybridization method apparently leaves the living cells unharmed. That is, in this hybridization method, the cells are not lysed or fixed, as in previous methods of nucleic acid hybridization, and are left apparently unharmed. Thus, cells or tissues can be characterized for the presence of a specific RNA or DNA sequence (referred to as the target sequence) without killing the cells. This is presumably because the probes eventually are degraded, diffuse out of the cell, or are diluted by newly synthesized target sequences. This procedure permits the selection of cells or subpopulations of cells based on gene expression or the presence of a target sequence. After hybridization, the cells of interest can be evaluated with respect to other parameters and segregated by methods such as microdissection or flow sorting. The selected cells can be cultured, further characterized or used as a source of RNA for the construction of cDNA libraries.

In vivo hybridization also permits the expression of a target sequence to be monitored over time and under inducing or inhibiting conditions. Thus, the causal relationships between biochemical or other regulatory factors (e.g. hormones, growth factors, oncogenes, stress conditions) and gene expression can be directly observed in a cell or tissue. The location and accumulation or degradation of a specific nucleic acid sequence can also be monitored. One application of this method is for optimizing antisense oligonucleotide pharmaceuticals. The method can be used to test various antisense oligonucleotide analogs for their ability to permeate cellular membranes and hybridize to the target DNA or RNA. This hybridization method provides a reliable method for locating a target nucleic acid sequence in a living cell or tissue.

Methods for modifying oligonucleotides in order to increase their ability to penetrate cell membranes are known in the art. Such modifications include replacement of phosphate backbone oxygens with, for example, sulfur or methyl groups, to decrease the hydrophilicity of the oligonucleotides and covalent attachment of chemical blocking groups at the 3'-end of the oligonucleotide. Some of these modifications also increase the resistance of the oligonucleotide probes to nucleases. Various detectable markers, labelling methods and methods of detection are also known in the art.

This invention also relates to a method of nucleic acid hybridization performed in vivo wherein the cells are fixed before detection and quantitation of specific hybridization within the cells. According to this method, modified and unmodified oligonucleotide probes are taken up rapidly and quantitatively by living cells, hybridize to complementary nucleic acids in the cells, and excess probes are washed from the cells. The cells are then fixed and detection and quantitation of specific hybridization is by in situ transcription assay. Reverse transcriptase extends a DNA primer hybridized to an RNA template. Thus, only hybridized oligonucleotides will prime incorporation of labeled nucleotide into new DNA to give a measurable signal in situ. This detection procedure modifies previous in situ transcription assays (Eberwine, J. et al., *Meth. Enz.* 216: 80–100 (1988); Mogensen, J. et al., *Exper. Cell. Res.* 196:92–98 (1991)) by allowing the primer to hybridize in vivo first and then assaying the hybridization in situ after permeabilization and fixation of the cell (Bassell, G. J. et al., *J. Cell. Biol.* 126: 863–876 (1994)). Thus, a signal generated by in situ transcription indicates specific hybridization of the probe in the living cell (i.e., that the probe hybridized to target nucleic acids in the living cell) and serves as a means to evaluate hybridization of probe in vivo.

BRIEF DESCRIPTION OF THE DRAWINGS

FIGS. 4A–4F are photomicrographs showing the results using in situ transcription to detect hybrids formed between S-oligo dT and poly (A) RNA in vivo. FIGS. 4A and 4B: Cultured cells were incubated in media containing 0.1 μM ST30 (FIG. 4A) or SA30 (FIG. 4B) for 2 hours, Triton extracted and fixed in formaldehyde/glutaraldehyde. IST was performed and incorporated dig-dUTP was detected using silver gold enhancement. FIGS. 4C and 4D: As in (FIGS. 4A and 4B) except ST30 (FIG. 4C) or SA30 (FIG. 4D) was added to cells after fixation (no oligo was added to live cells). FIG. 4E: Cells treated with ST30 in vivo but IST performed with heat inactivated RT mix. FIG. 4F: IST treated cells with no added oligo. Phase contrast micrographs, bar=20 microns.

FIGS. 5A–5D are photomicrographs showing that fluorescently-labeled O-oligo dT and S-oligo dT hybridize to RNA in vivo. Cells were incubated with 0.1 μM oligo for 2 hours, extracted, fixed and subjected to IST as described for FIGS. 4A–4F. Oligos used are: in FIG. 5A, Texas Red labeled O-oligo dT 43mer (T43tr); in FIG. 5B, the analogous dA (A43tr); in FIG. 5C, Texas Red labeled ST30 (ST30tr); and in FIG. 5D, SA30tr. Bar=20 microns.

FIGS. 6A–6B are photomicrographs showing detection of hybridization in unextracted cells. L6 cells were incubated with ST30tr for 2 hours, formaldehyde-fixed directly and subjected to IST. FIG. 6A depicts cells showing silver stain that represents hybridization of ST30tr to poly A RNA. FIG. 6B depicts the same cells showing fluorescent signal from internalized ST30tr. Bar=20 microns.

DETAILED DESCRIPTION OF THE INVENTION

Described herein is a method of nucleic acid hybridization that is performed in living cells (in vivo). The cells are not lysed or fixed, as in previous methods of nucleic acid hybridization, and are left apparently unharmed by the hybridization process, as determined by subsequent culture. The method is useful for detecting the presence, amount and location of a specific nucleic acid sequence (referred to as the target sequence) in individual cells or in tissues. The expression of a specific gene can also be assayed. The target nucleic acid sequence can be RNA or DNA. It can be in the nucleus, cytosol or an organelle of the cell. The target sequence can be native or foreign to the cell. For example, the presence of sequences specific to virus or bacteria infecting a cell or tissue can be detected. This method is applicable to various cell and tissue preparations, including cultured cells, suspended cells, cell monolayers, live tissue sections, and embryos.

This method employs unmodified and/or modified single-stranded oligonucleotides as probes, as defined below. The oligonucleotides have a sequence that is complementary to the target nucleic acid sequence. The oligonucleotides can be RNAs or DNAs in the approximate size range of 10–50 nucleotides, but a 15–30 nucleotide length is preferred for specificity and cost-effectiveness. The oligonucleotides can be chemically synthesized or isolated from natural sources by cloning, for example. The oligonucleotides which are, for example, chemically synthesized or isolated from natural sources by cloning consists of nucleotides which are covalently linked by phosphodiester groups. These oligonucleotides are referred to herein as phosphodiester-bonded oligonucleotides.

"Unmodified oligonucleotides" as defined herein are phosphodiester-bonded oligonucleotides and include phosphodiester-bonded oligonucleotides that are labelled with detectable markers, as described below, to allow for detection and quantitation of the oligonucleotides.

"Modified oligonucleotides" as defined herein are modified by known methods to increase their ability to penetrate hydrophobic cellular membranes. Such modifications include substitution of oxygens in the phosphate backbone to decrease the hydrophilicity of the oligonucleotides (Uhlmann and Peyman, *Chemical Reviews* 90 (4): 544–584 (1990); Goodchild, *Bioconjugate Chemistry* 1 (3): 165–187 (1990)). For example, one or more of the oxygens in the phosphate backbone can be replaced with sulfur to create phosphorothioate or a phosphorodithioate oligonucleotides (Marshall et al., *Proc. Natl. Acad. Sci. USA* 89: 6265–6269 (1991)) or with methyl groups to produce methylphosphonate oligonucleotides (Kean et al., *Biochem.* 27: 9113–9121 (1988)). Other oligonucleotide modifications include sulfone derivatives, formacetal derivatives, peptido-nucleic acids, bicyclo derivatives and methylene acetal derivatives (e.g. Jones et al., NAMA conference, CANCUN, January 1993, p.27; Nielsen et al., *Science* 254: 1697 (1991); Jablonski et al., *Nucleic Acids Res.* 14: 6115 (1986); Smith et al., *Nucleic Acids Res.* 13: 2399 (1985)). In addition, oligonucleotides can be modified by covalent attachment of chemical blocking groups to their 3'-ends. Such 3' blocking groups include amino-modified nucleotides, methyl blocking groups, fluorochrome-conjugated groups, 3' to 5' nucleotide linkages, and succinyl ester groups (e.g. Zerial et al., *Nucleic Acids Res.* 15: 9909 (1987); Li et al, *Nucleic Acids Res.* 15: 5275 (1987); Zuckerman et al., *Nucleic Acids Res.* 15: 5305 (1987)).

Some of these phosphate backbone and 3'-end blocking modifications also render the oligonucleotides more resistant to cellular nucleases, thus, increasing the effective concentration of the probe in the cell. The probes can be further modified to optimize their speed of penetration into and exit from the cell.

The modified and unmodified oligonucleotides are labelled with detectable markers. A variety of markers and labelling methods are known in the art, including fluorescent, chemiluminescent, biotin, radioactive, enzymatically detected, and immunologically detected markers (Smith et al., *Nucleic Acids Res.* 13 (7) : 2399–2412 (1985); Agrawal et al., *Nucleic Acids Res.* 14 (15): 6227–6245 (1986); Cook et al., *Nucleic Acids Research* 16 (9): 4077–4095 (1988); Kumar et al., *Anal. Biochem.* 169: 376–382 (1988); Taneja and Singer, *J. Cellular Biochem.* 44: 241–252 (1990); Jablonski et al., *Nucleic Acids Res.* 14 (15): 6115–6128 (1986); Tomlinson et al., *Anal. Biochem.* 171: 217–222 (1988)). Fluorescent labelling, which permits quantitation of hybridization and selection of cells by flow sorting, is preferred. Methods and apparatuses for detection and quantitation of labelled probes are known in the art, including fluorescent microscopy, flow cytometry and image analysis techniques (Lawrence and Singer, *Seminars in Cell Biology* 2: 83–101 (1991); Taneja et al., *J. Cell Biol.* 119 (5): 1245–1260 (1992)).

The term "probe" refers to either modified oligonucleotides, unmodified oligonucleotides, mixtures of each or combinations of both.

Various embodiments of the method are useful for detecting the presence of a target nucleic acid sequence in a living cell or tissue. One embodiment comprises incubating the cell or tissue with a probe under conditions suitable for specific hybridization of the probe to complementary nucleic acid sequences in the cell or tissue, washing the cell or tissue to allow the excess unhybridized probe to exit the cell(s), and detecting specific hybridization of the probe, which indicates the presence of the target sequence in the cell or tissue. The conditions of hybridization, including concentration of probe, time of hybridization and time of washing, depend on the abundance of target sequence and can be determined empirically through routine experimentation. Preferably, the minimum concentration of probe required to detect specific hybridization in a reasonable amount of time is used. This has been found to be lower by at least three orders of magnitude than the concentrations currently used in the art to obtain inhibition of expression by antisense oligonucleotides. Typically, the higher the concentration of probe, the less incubation time required for hybridization, and vice versa. Too high a concentration of probe, however, increases nonspecific background and is toxic to the cell. Optimization of these conditions can be done by routine experimentation.

The probe is added in a physiological medium acceptable to the cells, such as cell growth medium (preferably without serum). Unlabelled probe with a different sequence can also be added, either with the labelled probe or in the wash medium to reduce nonspecific hybridization. Appropriate positive and negative controls should be performed.

In a preferred embodiment, living cells are incubated in medium containing 10 to 100 nM fluorochrome-labelled modified DNA probe for about two minutes. The medium is removed, fresh medium is added, and the cells are washed for about 1 to 2 hours. Less incubation and wash times may be required depending on the abundance of the target sequence and the concentration of the probe. The cells can then be observed by microscopy and the amount of hybridization quantitated by fluorescence measurements. In cultured chick embryo fibroblasts hybridized under these conditions, target mRNAs in the cytoplasm and nucleus were observed to be hybridized to probe by fluorescence microscopy. Excess probe had exited from the cells after about 1 to 2 hours incubation in medium. No toxic effects on the cells were observed after three days, as the cells continued to divide.

Figure 1:
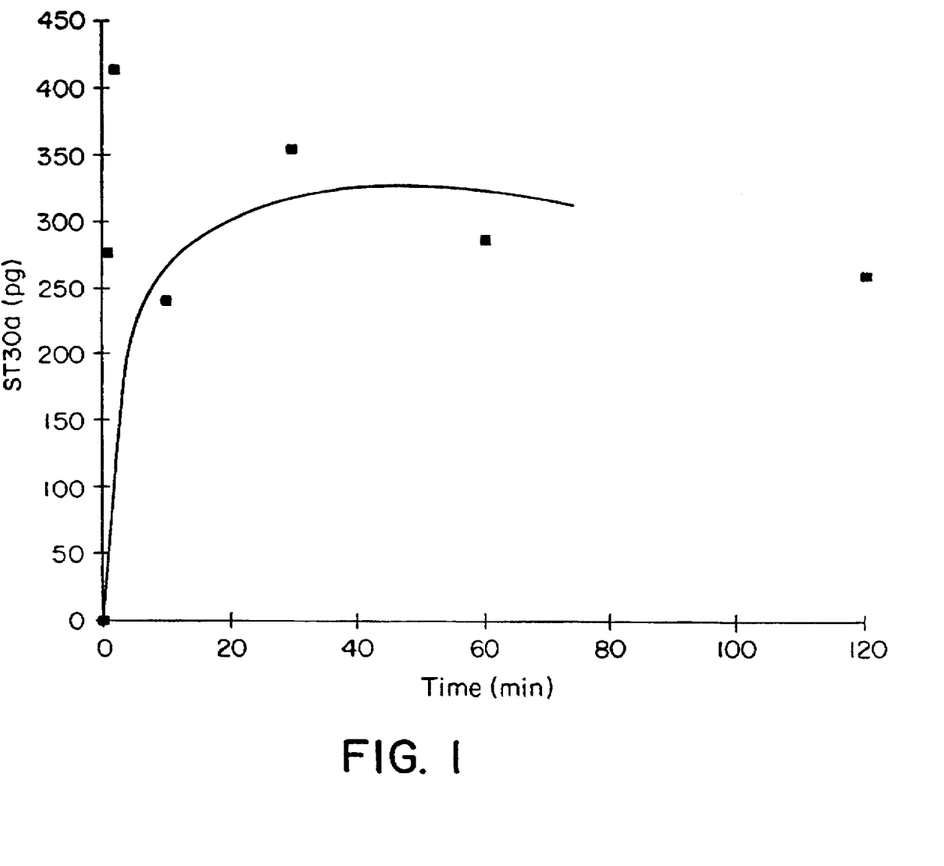
FIG. 1 is a graphical representation showing the uptake of the probe $^{32}$P-ST30a into living human fibroblast cells.
Figure 3:
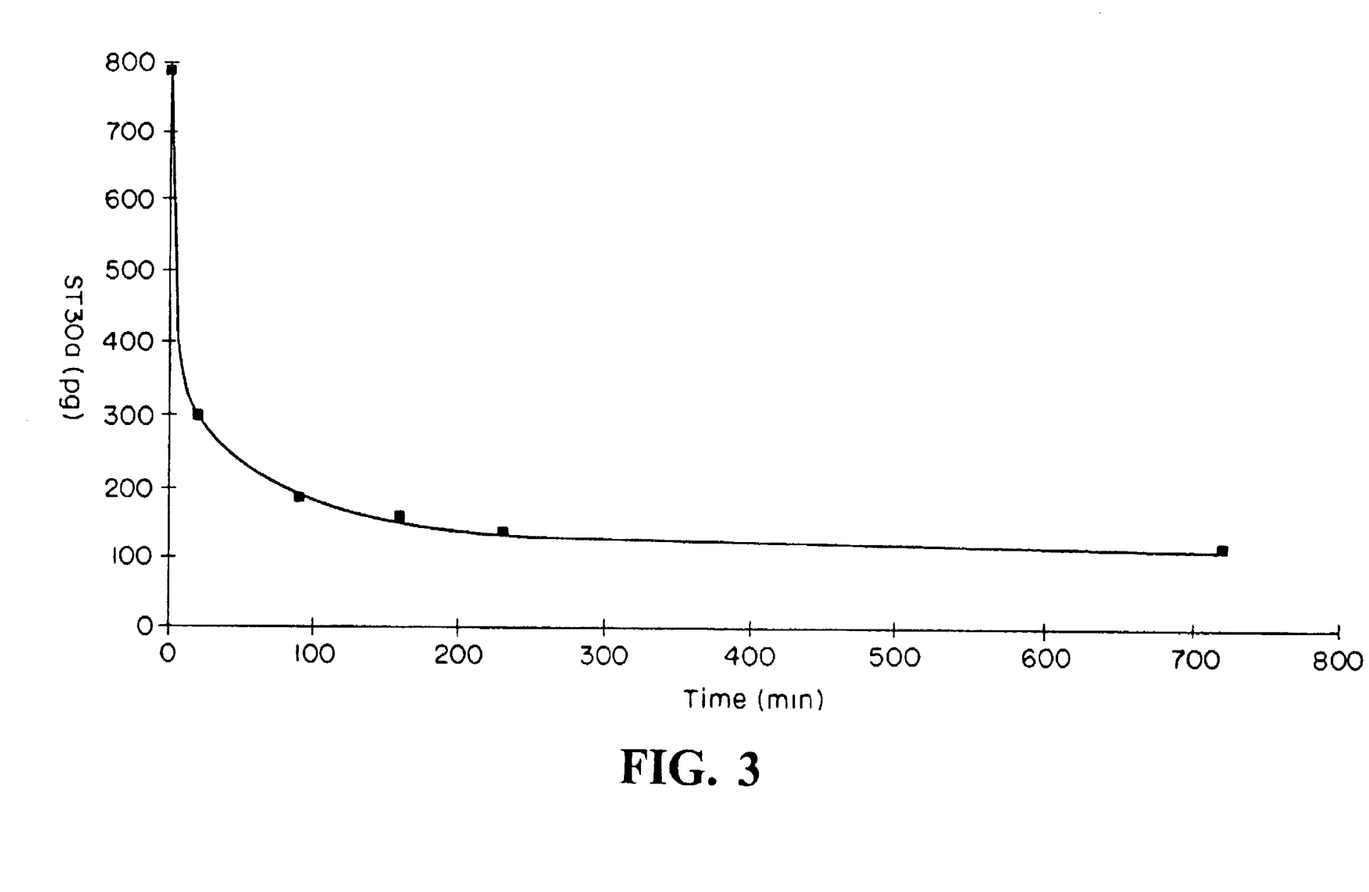
FIG. 3 is a graphical representation showing the efflux of the $^{32}$P-ST30a probe from living rat myoblast (L6 cells) cells during the wash step.

Rapid equilibration of intracellular probe concentrations with extracellular probe concentrations has been demonstrated (FIG. 1; Example 5). The intracellular concentration of probe reached saturation level in about 15 minutes. This suggests a passive entry mechanism of cell uptake rather than endocytosis, which takes hours. It has also been demonstrated that most of the probe was able to exit the cells during the wash step, apparently also by passive diffusion (FIG. 3; Example 7). The intracellular probe concentration reached equilibrium after about 2 hours wash. A small fraction of probe remained in the cells, presumably retained there by hybridization to target sequences, which was visualized microscopically (Example 7). Thus, the in vivo hybridization can be performed in a sufficiently short amount of time so as to be convenient and feasible with living cells.

This method of hybridization can be used to quantitate the amount of a particular target sequence in the cell. As described in Example 7, conditions for hybridization can be used such that essentially all target sequences in the cell are saturated with probe. In this example, hybridization with a phosphorothioate probe blocked any subsequent hybridization with probes complementary to the same target sequence.

In addition, the hybridization method can be performed using two or more differentially labelled probes simultaneously. That is, each probe has a nucleotide sequence complementary to different target nucleic acids. For example, the expression of two different genes can be monitored in the same cell using probes labelled with different colored fluorochromes.

The hybridization method can also be performed using a probe that is relatively nuclease-sensitive but remains intact long enough in the cell to hybridize to target sequences, whereupon, in this double-stranded form, it becomes nuclease-resistant, while unhybridized probe is degraded. That is, a probe which is nuclease-sensitive is hydrolyzed by nucleases; a probe which is nuclease-resistant is not hydrolyzed by nucleases. As a result, it is less necessary to incubate the cells in medium to wash out unhybridized probe; the cells can be quickly rinsed to remove extracellular probe.

The hybridization method can also be performed using energy transfer to detect the hybridization. In this case, two oligonucleotides, one labelled with an energy donor group and one labelled with an energy acceptor group, comprise the probe. The two oligonucleotides can be modified, unmodified or a combination of both. The two oligonucleotides have sequences such that they hybridize to immediately adjacent sites on the target sequence. The oligonucleotide with its 5' end closest to the 3' end of the second oligonucleotide when hybridized to immediately adjacent sites on the target nucleic acid sequence is labelled on the 5' end with either an energy donor group or an energy acceptor group; the second oligonucleotide is labelled on the 3' end with whichever group, either an energy donor group or an energy acceptor group, not used as a label on the first oligonucleotide. When the two oligonucleotides are brought near each other due to hybridization to the target sequence, energy transfer takes place between them. When two fluorophores whose excitation and emission specta overlap are in sufficient close proximity, the excited state energy of the donor molecule is transferred to the neighboring acceptor fluorophore. The result is quenching of donor fluorescence, an enhancement of acceptor fluorescence intensity. The cells are irradiated with light at an excitation wavelength, energy transfer occurs, and the emitted light is detected by increase in fluorescence intensity (see, e.g. Cardullo et al., *Proc. Natl. Acad. Sci. USA* 85: 8790–8794 (1988)).

Living cells were shown directly to take up synthetic antisense oligonucleotides (oligos) and these probes hybridize to intracellular RNA. The kinetics of uptake and egress were measured using fluorescently-labeled oligos and digital imaging analysis of fluorescent intensity as a function of time. Hybridization in vivo was demonstrated by the ability of oligos added to cultured cells to prime a reverse transcriptase reaction in situ. Both S-oligo (phosphorothioate modified oligo) dT, and fluorescently-labeled O-oligo (phosphodiester-bonded oligo) dT, but not S- or O-oligo dA, acted to prime in situ incorporation of labeled deoxyribonucleotide triphosphates by reverse transcriptase.

These results provide a direct demonstration that oligos passively internalized by cells hybridize to their intracellular target, thus providing a means to assess whether cellular changes induced by antisense treatments result from specific hybridization of an oligo to its mRNA target or from other undefined effects.

Fluorescent S-oligo dT was detected in nuclei as well as the cytoplasm in approximately 30% of the cells. In these cells, the DNA dye, 4′, 6-diamidino-2-phenylindole (DAPI), was twice that in unlabeled nuclei, suggesting that the nuclear signal could be cell cycle dependent. Oligo uptake is cell cycle dependent in other cell types (Vlassov, V. V. et al., *Biochim. Biophys. Acta* 1197: 95–108 (1994); Zamecnik, P. et al., *Proc. Natl. Acad. Sci. USA* 91: 3156–3160 (1994)) and nuclear envelope permeability changes throughout the cell cycle and varies between quiescent and dividing cell populations (Feldherr, C. M. et al., *Internat. Rev. of Cytol.* 151: 183–228 (1994)). When S- or O-oligo dT treated cells were evaluated using in situ transcription, about the same fraction (30%) of cells showed silver stained nuclei, indicating hybridization of probe to poly (A) targets. Nuclear signal was not observed using fluorescent S-oligo dA. This could be due to differences in transport or to a lack of intranuclear hybridization targets.

In vivo hybridization occurred despite probable competition with RNA-binding proteins. For instance, poly (A) binding proteins are known to interact with the poly (A) tails of mRNAs (Sachs, A., *Curr. Opin. Cell. Biol.* 2: 1092–1098 (1990)). Nonetheless, the results show exogenous oligo dTs hybridized to these sequences in vivo. Thus, it is reasonable to predict that antisense oligos have a higher affinity of binding to their specific sequences than proteins and can interfere with protein/RNA interactions in the cell. Alternatively, the oligo dT may hybridize to poly (A) RNA that is not covered by protein.

It also appears that oligo dT hybridization in vivo does not disrupt poly (A) mRNA association with the cytoskeleton. The pattern of hybridization after oligo treatment in vivo was very much like the overall pattern detected when primers were added after, instead of before, cell fixation. Since both cell populations were Triton extracted before fixation, the signal detected after in vivo hybridization was generated from Triton insoluble priming sites, presumably oligo dT/mRNA hybrids associated with the cytoskeleton. Although the extent of oligo dT hybridization along the poly (A) tail is not known, hybrids large enough to prime RT do not disrupt interactions poly (A) may have with the cytoskeleton (Taneja, K. L. et al., *J. Cell. Biol.* 119: 1245–1260 (1992)). These results support the idea that oligos can be used as tags to follow mRNA movement without affecting mRNA localization in vivo. Further, the simple ability to elongate an oligo primer using reverse transcription suggests that RNase H activity (Wintersberger, U., *Pharmac. Ther.* 48: 259–280 (1990)) in these cells was not sufficient to destroy RNA/DNA hybrids formed with exogenous oligo dT.

Utility of the Invention

A major advantage of this hybridization method is the ability to detect nucleic acid sequences or evaluate gene expression in a cell or tissue without killing it. The cells of interest are still available after hybridization for further observation and characterization. Thus, cells can be selected based on the expression of any known gene sequence, i.e. presence of the target sequence among the cellular RNAs. The genes can be chromosomal, mitochondrial or chloroplastic, episomal, viral or transfected. For many applications, quantitation of the detected cells is sufficient. However, hybridization can also be followed by physical segregation of the cells of interest by known methods, such as fluorescence activated cell sorting or microdissection. The isolated subpopulation can then be cultured as a subclone or used as a source of RNA for cDNA library construction.

A second advantage of this method is that it adds a temporal dimension to the diagnostic capabilities of nucleic acid hybridization. The expression of a specific gene can be monitored over the course of a cell's or tissue's differentiation or development. The hybridization method can be performed repeatedly on a population of cells without damaging the cells. The effect of regulatory factors, such as other genes, hormones, differentiation, growth protein factors, and environmental conditions, on the expression of specific genes in a cell or tissue can be observed directly. For example, the induction of the transformed phenotype by expression of an oncogene can be directly observed. This method obviates the often difficult task of obtaining homogeneous and synchronized cell populations for studies on gene expression. Since hybridization of the DNA probe may result in destruction of the endogenous RNA by endogenous RNAse H, which digests the RNA in DNA-RNA duplexes, the cellular response to destruction of this RNA could be monitored directly.

The in vivo method is expected to be more informative than previous hybridization methods for locating target nucleic acids in cells or tissues, since live cells are used in the assay. In addition, the method is quicker and simpler than hybridization methods requiring pretreatment of the cells with fixatives, and subsequent in situ hybridization, which can take hours.

This method is also useful for determining the presence of specific DNA sequences in cells. In this case, the single-stranded probe forms a triple helix (C≡G≡C or T≡A≡T) with the target double-stranded DNA. For example, retroviral sequences, such as from the Human immunodeficiency Virus (HIV), can be visualized and their presence in the chromosome (e.g. at the site of transcription) or in nuclear or cytoplasmic RNA can be monitored. Gross chromosomal deletions, additions and translocations may also be identified by triple helix formation, for example, for diagnosis of trisomy 21 in Down's Syndrome or deletions in the X-chromosome in muscular dystrophy, where the loss of hybridization signal to dystrophin would indicate the loss of the mRNA or the gene. The presence and movements of infectious agents (viral, bacterial, mycoplasma) and parasites, or their nucleic acids, can also be observed in tissues and organs. Movements of chromatin can be monitored during changes in cell behavior (e.g. transformation) or during development.

In addition, the in vivo hybridization method is useful for assessing and optimizing pharmaceuticals based on antisense oligonucleotides. Antisense nucleotides are currently being developed, for instance, as an anti-HIV therapy. It is known in the art that some antisense probes or procedures are unsuccessful or inefficient. The ability to visualize these molecules in vivo would aid in the analysis of parameters and molecule design that are important for successful inhibition of HIV. For example, the ability of various antisense probes to enter the nucleus and hybridize to sequences in the cell can be empirically assessed.

The following examples, which are not intended to be limiting in any way, more specifically illustrate the invention.

EXAMPLE 1

Synthesis of Fluorochrome-Labelled Phosphorothioate Probes

Oligonucleotide (30 nucleotides) probes containing phosphorothioate linkage in each position (i.e., sulfur replaces one oxygen at every phosphodiester bond) were made on the Applied Biosystem DNA Synthesizer 394 (Foster City, Calif.) with amino-modified linker thymidines (Jablonski, E. et al., *Nucleic Acids Res.* 14: 6115 (1986)) added at the second positions from the 3'- and 5'-ends. After purification by chromatography on Sephadex G50, the DNA was labelled with fluorochromes (Texas red, Cy3 or FITC) in $NaHCO_3/Na_2CO_3$, pH 9.0, overnight at room temperature in the dark (Molecular Probes, Eugene, Ohio). Labelled oligonucleotides were purified by electrophoresis on 10% polyacrylamide gel under non-denaturing conditions and eluted from the appropriate bands.

ST30 is a 30 nucleotide (nt) homopolymer of thymidine where sulfur replaces one oxygen at every phosphodiester bond (S-oligo). This homopolymer was labeled at positions 2 and 29 using texas red (Molecular Probes) (ST30tr). S-oligo dA served as controls for STS30 and ST30tr and were designated SA30 and SA30tr, respectively.

EXAMPLE 2

Synthesis of Fluorochrome-Labelled Phosphodiester-Bonded Probes

Oligonucleotides were synthesized using an Applied Biosystems 394 DNA Synthesizer. Fluorochromes were covalently linked to oligos at specific aminated thymidines and fluorochrome-conjugated oligos purified through two Sephadex G-50 columns before use as described in Example 1. The O-oligo, T43tr, is a 43 nucleotide homopolymer of thymidine with texas red covalently linked to positions 2, 12, 22, 32 and 42. A43tr is the comparable oligo dA control for T43tr; T43f and A43f are identical to T43tr and A43tr, respectively, except that fluorescein (Molecular Probes) is substituted for texas red.

Oligo concentrations were calculated assuming 1 $OD_{260}$ unit=33 µg/ml. To take into account the differences between oligo dA and oligo dT molar extinction coefficients, oligo dT concentrations should be increased 30%.

EXAMPLE 3

Cell Extraction and Fixation

Cells on coverslips were fixed directly in 4% formaldehyde in 1 mM $KH_2PO_4$, 10 mM $Na_2HPO_4$, 0.137M NaCl, 2.7 mM KCl, pH 7.0 (PBS) and 5 mM $MgCl_2$. For most in situ transcription (IST) experiments, cells were Triton extracted as follows before fixing. Cells were washed in cytoskeletal extraction (CSK) buffer (0.3M sucrose, 0.1M KCl, 5 mM $MgCl_2$ 10 mM PIPES, pH 6.9, 2 mM EGTA, 1 µg/ml leupeptin (Sigma) and 1 µg/ml trypsin inhibitor (Sigma)) at 4° C. and then extracted with 0.5% Triton in CSK buffer for 90–120 seconds. Extractions were routinely done at 4° C. where maximal RNA retention (and hybridization signal) is observed (Bassell, G. J. et al., *J. Cell. Biol.* 126: 863–876 (1994)). At this temperature, microtubules may dissociate, so cells were also extracted at room temperature and analyzed as described herein. No obvious difference in the distribution of signal was observed. After washing with CSK buffer, cells were fixed with 4% formaldehyde, 0.1% glutaraldehyde, 5 mM $MgCl_2$ in PBS for 15 minutes at room temperature. Coverslips were then rinsed twice with 70% ethanol and stored in same at 4° C. for up to three months.

EXAMPLE 4

Microscopy and Image Analysis

Coverslips containing cells to be viewed were mounted in Vectashield (Vector Labs) containing 0.1 µg/ml 4', 6-diamidino-2-phenylindole (DAPI). Silver stained or fluorescent cells were viewed and photographed using a Nikon Microphot SA equipped with bright field and fluorescence optics and a 35 mm camera. Some fluorescent images were captured using a Photometrics CCD camera, visualized on a monitor and digitized areas of signal individually segregated for quantitation using software provided by the Biomedical Imaging Center at University Massachusetts Medical School (Taneja, K. L. et al., *J. Cell. Biol.* 119: 1245–1260 (1992)). To automate image digitation and quantitation, a digital imaging workstation sold under the trademark "DISCOVERY"(Becton Dickinson Cellular Imaging Systems, San Jose, Calif.). To quantify silver-staining, a microscopic field image was captured with a Xillix Microimager 1400 gray-scale camera using a 500 nm interference filter in absorbance mode. In real time, cells were automatically identified using standard image processing routines to segment objects and morphological filters to eliminate artifacts. Image thresholds were selected automatically based on the standard deviation of the field image pixel intensity histogram. The instrument verified segmented objects were cells by superimposing a similarly segmented image that was captured using a fluorescent light source with a DAPI filter set. Optical density of the silver stained cell was then automatically calculated and images captured for later inspection. Fluorescence in cells containing Texas Red or fluorescein labeled oligos was also measured automatically using the appropriate filters and similar segmentation programs. Raw data (mean fluorescence/cell or $A_{500}$/cell) was converted to percent maximal signal/cell in any given experiment so that data from separate experiments could be averaged. Error bars represent standard error of the mean and fall underneath plot symbol if not visible.

EXAMPLE 5

Quantitative Analysis of Probe Uptake into Cells

The kinetics of uptake of modified single-stranded oligonucleotide probes into living cells was examined using a phosphorothioate poly(dT) oligonucleotide of thirty nucleotides length, referred to as ST30a. This oligonucleotide was synthesized, as described in Example 1, with an amino linker for fluorochrome attachment. For the purposes of this experiment, however, the oligonucleotide was labelled with $^{32}$P. The poly(dT) is expected to hybridize intracellularly to the poly (A) tracts of the mRNAs in the cell. Approximately 20,000 human fibroblast cells were exposed to an extracellular concentration of 0.1 µM of the $^{32}$P-labelled probe for 2 hours and the intracellular concentration of the probe determined after 0, 2, 5, 10, 30, 60 and 120 minutes incubation (FIG. 1). The intracellular probe concentration was determined by measuring the Cerenkov radiation of the cells (after rinsing them) in a scintillation counter.

As shown in FIG. 1, cells took up the $^{32}$P-ST30a probe very rapidly in the first about 5 minutes, reaching saturation in about 15 minutes. The peak intracellular concentration of probe was about 280 pg per 20,000 cells or 0.1 µM. The rapidity with which the internal probe concentration equilibrated with the extracellular probe concentration (less than 10 minutes) suggests that the oligonucleotide probes go into the cell passively, rather than by endocytosis, which takes hours, as previously reported.

The intracellular concentration of probe can be calculated as follows:

280 pg probe/20,000 cells=approx. $10^{-2}$ pg/cell. Given that 1 cell=approx. 10 pl, $10^{-2}$ pg/cell=$10^{-2}$ pg/10 pl=$10^{-3}$ pg/pl=0.1 µM.

The volume per cell is calculated as follows:

Diameter of one cell=approx. 20 microns.

Volume of one cell=approx. $(20\mu)^3 = 10^4 \mu^3 = 10$ pl.

In another experiment, L6 rat muscle cells (American Tissue Culture) were cultured using standard techniques in Dulbecco's modified Eagle's media (DMEM) containing 10% fetal bovine serum (FBS, heat-inactivated). Cells to be treated with oligos were first trypsinized and then plated onto 12 mm round glass coverslips (boiled previously in 0.1N HCl, rinsed and autoclaved, Fisher), in 24-well dishes (Falcon) containing DMEM plus 10% FBS. Cells were plated at a density of 25–35,000 cells per coverslip and allowed to grow 20–28 hours at 37° C., 5% $CO_2$. The media was then replaced with 250 µl fresh DMEM containing oligos for varying times at 37° C., 5% $CO_2$. For efflux experiments, oligo-containing media was removed, cells were washed 3 times and then incubated with 250 µl serum-free DMEM.

Figure 2A:
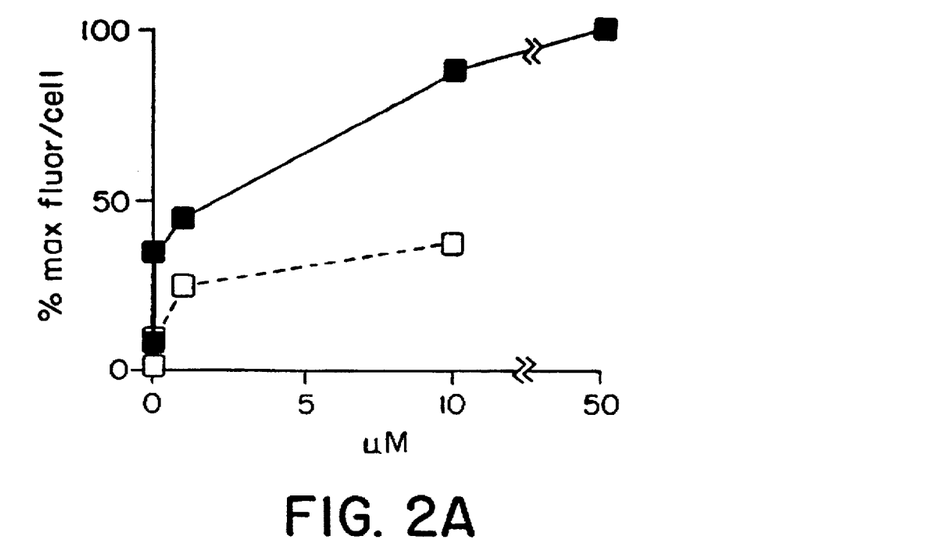
FIG. 2A is a graphical representation showing the uptake of the probes ST30tr (-■-) and SA30tr (-□-) into living L6 cells as a function of probe concentrations.
Figure 2B:
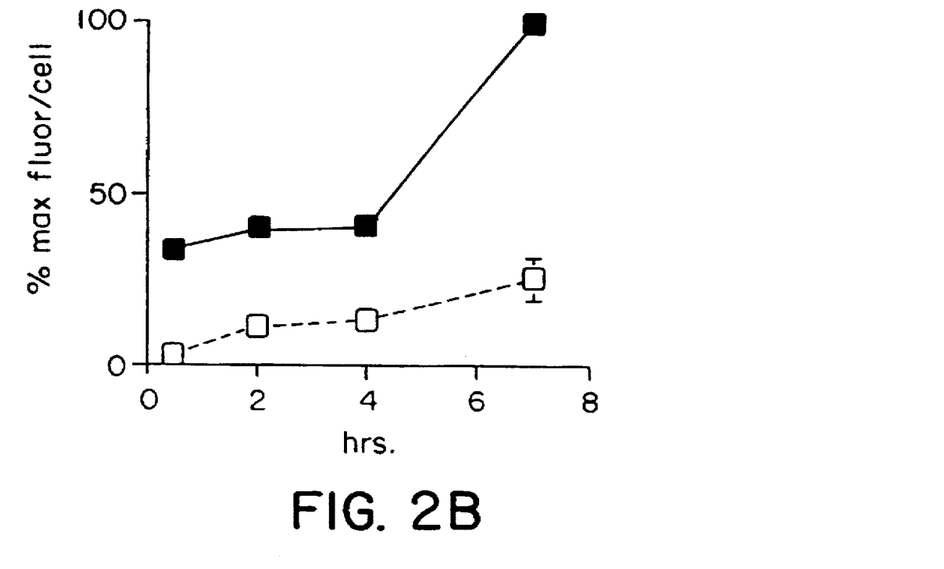
FIG. 2B is a graphical representation showing the uptake of the probes ST30tr (-■-) and SA30tr (-□-) into living L6 cells as a function of incubation time.
Figure 2C:
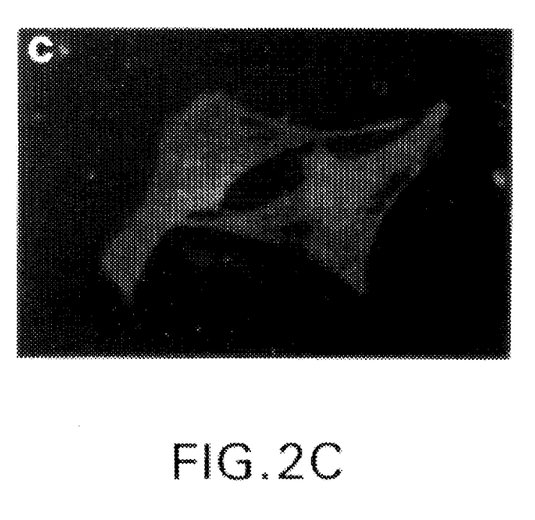
FIG. 2C is a photomicrograph showing distribution of fluorescence in L6 cells after incubation with probe ST30tr.
Figure 2D:
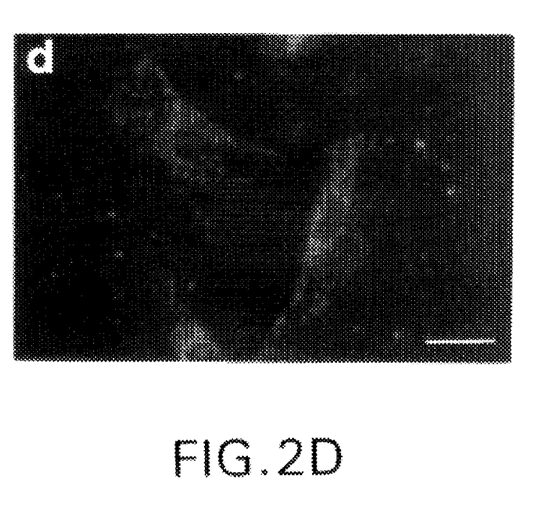
FIG. 2D is a photomicrograph showing distribution of fluorescence in L6 cells after incubation with probe SA30tr.

Varying amounts of Texas Red labeled poly dT (ST30tr) or dA (SA30tr) S-oligos were added to cells growing on glass coverslips and cells were incubated for varying amounts of time. Cells were washed, formaldehyde-fixed and intracellular fluorescence digitized. Digital imaging microscopy was used to characterize the uptake of fluorescently-labeled oligos by L6 cells. As shown in FIGS. 2A and 2B, intracellular fluorescence increased with either increasing extracellular concentration or increasing incubation times. Intracellular fluorescence was saturated when incubated at oligo concentrations of 10 µM for 2 hours. S-oligo dT showed primarily a punctate perinuclear distribution with additional diffuse fluorescence throughout the cell (FIG. 1C). Nuclei were labeled more intensely than cytoplasm in about 30% of the cells. When S-oligo dA was incubated with cells under these same conditions, intracellular labeling was about half of that observed with S-oligo dT (FIGS. 2A and 2B). No nuclear labeling was observed but a similar punctate cytoplasmic distribution of label was present (FIG. 1D).

S-oligos labeled with different fluorochromes (fluorescein or cy3) showed labeling patterns similar to that described above and similar results were obtained in a different cell line (human fibroblasts) exposed to ST30tr or SA30tr. It is reasonable to predict that S-oligo dT is sequestered more effectively than S-oligo dA in these cell types and that the nature of the fluorochrome label does not appreciably affect the cellular compartments labeled.

As a result of these experiments, a standard incubation time of 2 hours and concentration of 0.1 µM were chosen for further experimentation. Under these conditions, extracellular probe concentration was at least 1000 fold excess of the target poly (A) RNA concentration, intracellular fluorescence was reproducible and cell morphology and growth characteristics were not detectably affected by oligo treatment. At high (50 µM) concentrations, vacuolation and cell death sometimes occurred, most frequently with S-oligo dA.

FIGS. 2A and 2B show the uptake of fluorescently-labeled S-oligo dT and dA by L6 cells. Cells were incubated with ST30tr (-■-) or SA30tr (-□-) in serum-free media, formaldehyde fixed and intracellular fluorescence quantitated. Plots show fluorescence/cell after incubation for 2 hours with varying oligo concentration (FIG. 2A) or with 0.1 µM oligo for varying amounts of time (FIG. 2B). Bar=20 microns.

EXAMPLE 6

Exit of the Probe from Cells

The ability of the probe to exit cells was examined by incubating about $5 \times 10^4$ rat L6 myoblasts in about 0.1 µM $^{32}$P-ST30a for about 10 minutes, removing the probe, and washing the cells in fresh medium without probe. FIG. 2 shows the amount (pg) of intracellular probe during washing of the cells. After about 2 hours, the intracellular probe dropped to an equilibration level of about 100 pg or $5 \times 10^{-5}$ pg/cell. This experiment shows that a majority of the probes entering the cells exited the cells during the wash. It is reasonable to conclude that the nonequilibrating fraction of probe (about 100 pg) is retained in the cells by hybridization to target sequences.

In order to saturate target sequences in the cells, the hybridization experiment was also performed with 15 µM of unlabelled ST30a containing a tracer amount (0.1 µM) of the $^{32}$P-labelled probe. As before, cells were incubated with probe for 10 minutes, the probe removed, and the cells washed with fresh medium for 2 hours. A separate experiment comprising a 30 minute incubation with probe and 2 hour wash was also performed with similar results. After the wash, both experiments yielded a final intracellular concentration of about 38 pg probe within the cells. These numbers correlate well with the expected amount of poly (A) target sequences within the cell, about 100,000 molecules. Since the oligonucleotide is 30 nt long, 30×330 (mol. weight of one mole of nucleotide)=$10^4$ grams/mole of oligonucleotide. Therefore, about 40 picograms in 20,000 cells=$40 \times 10^{-12}$ g, or $20 \times 10^{-16}$ g in one cell. Since $10^4$ grams=$6 \times 10^{23}$, one oligonucleotide=$0.16 \times 10^{-19}$ g. Therefore, $20 \times 10^{-16}$ g/$0.2 \times 10^{-19}$ g=100,000 molecules hybridized per cell. This is very close to a complete hybridization of intracellular targets.

EXAMPLE 7

Microscopic Analysis of In vivo Hybridization

A direct observation of hybridization of the probes within cells was made by fluorescent microscopy. Cells were exposed to a red fluorochrome-conjugated phosphorothioate poly(dT) (30 nucleotides long) probe. Hybridization was carried out, with 10 minutes incubation in 1 µM probe and 2 hours wash. After the wash, the cells were fixed and examined by fluorescent microscopy. Red fluorescence was observed in the nucleus and diffusely throughout the cytosol of the cells, indicating hybridization of the probes to RNAs in the nucleus and cytosol of the cells (Lawrence and Singer, *Seminars in Cell Biol.* 2: 83–101 (1991); Taneja and Singer, *J. Cell Biochem.* 44: 241–252 (1990); Taneja et al., *J. Cell Biology* 119 (5): 1245–1260 (1992)).

The fixed cells were further hybridized to a green poly (dT) probe (not a phosphorothioate). Hybridization of the fixed cells was carried out with 1 µM green probe in 2× SSC, 15% formamide for 1 hour and washed three times for 5 minutes each. No hybridization of the poly(dT) probe was detected, indicating that the target sequences were not available for hybridization, i.e. they were already hybridized to the red probe.

In a control experiment, in vivo hybridization to a phosphorothioate poly(dC) (30 mer) did not block subsequent hybridization with the poly(dT) green probe, indicating that the hybridization observed with the phosphorothioate poly (dT) probe was sequence specific. These results demonstrate that sequence specific hybridization can be performed in vivo.

EXAMPLE 8

In Situ Hybridization

In situ hybridization was performed in 10% formamide, 2×SSC (SSC is 150 mM NaCl, 15 mM NaCitrate, pH 7.0) at 37° C. with other additions and washes as described (Kislauskis, E. H. et al., *J. Cell. Biol.* 123: 165–172 (1993); Taneja, K. L. et al., *J. Cell. Biol.* 119: 1245–1260 (1992)) except that formamide was omitted when S-oligos were present. In some experiments where cells were incubated with oligo and then subjected to in situ hybridization, 100 µg/ml puromycin was added to the media. No difference in the amount of subsequent in situ hybridization was seen in these cells as compared to cells treated with oligo in the absence of puromycin.

EXAMPLE 9

In Situ Transcription (IST)

Cells which had been exposed to various oligos in vivo and then fixed as described above were washed in PBS for 10 minute, and then twice in 150 mM NaCl, 15 mM NaCitrate, pH 7.0 (SSC) for 10 minute each time. Samples were then treated with AMV reverse transcriptase (Promega) essentially as described (Eberwine, J. et al., *Meth. Enz.* 216: 80–100 (1988); Bassell, G. J. et al., *J. Cell. Biol.* 126: 863–876 (1994)) except that the buffer supplied by Promega was used. Digoxigenin (dig) or biotin labeled dUTP (Boeringer-Mannheim) or biotin labeled dCTP (Enzo Biochemicals; biotin is linked to carbon 5 on cytidine) was used at 50 µM in addition to all four unlabeled deoxynucleotides (Pharmacia) at 250 µM in the reaction mixture. Label was visualized using either sheep antidigoxigenin antibodies linked to 1 nm gold particles (SAD1) or goat antibiotin antibodies linked to 1 nm gold particles (GAB1) followed by silver enhancement (Amersham) (Bassell, G. J. et al., *J. Cell. Biol.* 126: 863–876 (1994)). Both antibodies were from Goldmark Laboratories. Control cells in which primers were added in situ were also subjected to IST. Formamide was omitted from all hybridization solutions containing S-oligos.

It was postulated that the uptake of the S-oligo dT probe by live cells would result in hybridization to cellular poly (A) in vivo. To test this hypothesis, it was reasoned that the resulting oligo-RNA hybrid would be capable of priming elongation by reverse transcriptase (RT) in situ. Because RT extends a DNA primer hybridized to an RNA template, only hybridized oligos prime incorporation of labeled nucleotide into new DNA to give a measurable signal in situ. This detection procedure modifies previous in situ reverse transcription (IST) assays (Eberwine, J. et al., *Meth. Enz.* 216: 80–100 (1988); Mogensen, J. et al., *Exper. Cell. Res.* 196: 92–98 (1991)) by allowing the primer to hybridize in vivo first and then assaying the hybridization in situ after permeabilization and fixation of the cell (Bassell, G. J. et al., *J. Cell. Biol.* 126: 863–876 (1994)). Digoxigenin (dig) labeled nucleotides were used in the RT reaction mixture and after incorporation were detected by sheep anti-digoxigenin (SAD1) antibodies linked to 1 nm gold particles. The gold was then enhanced by silver deposition (Bassell, G. J. et al., *J. Cell. Biol.* 126: 863–876 (1994)).

Figure 4A:
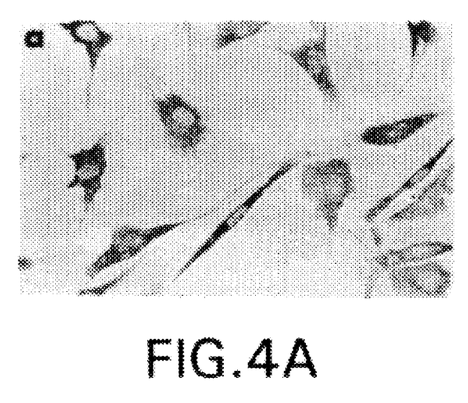
Figure 4B:
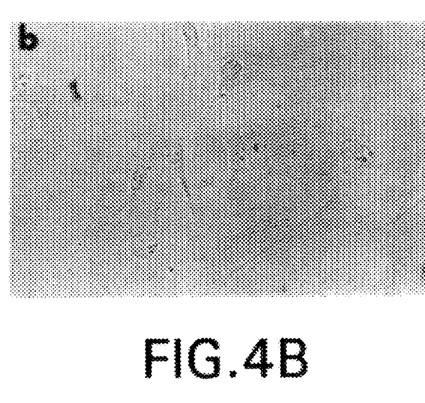
Figure 4C:
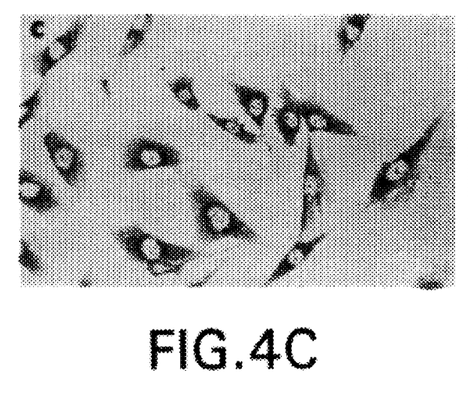
Figure 4D:
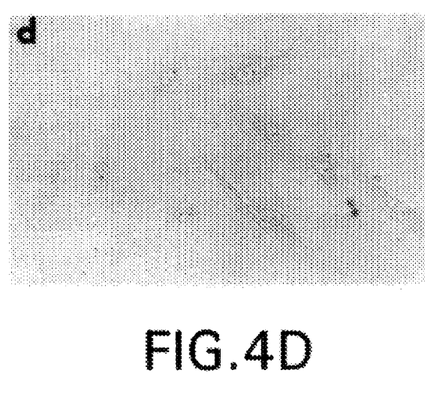
Figure 4E:
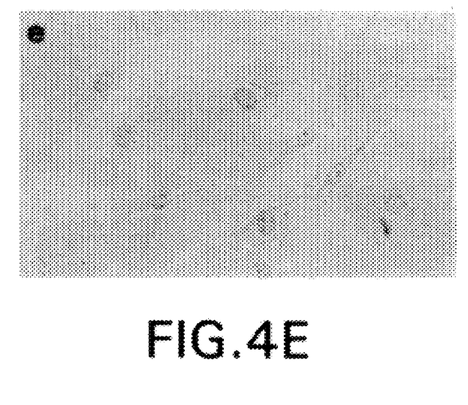
Figure 4F:
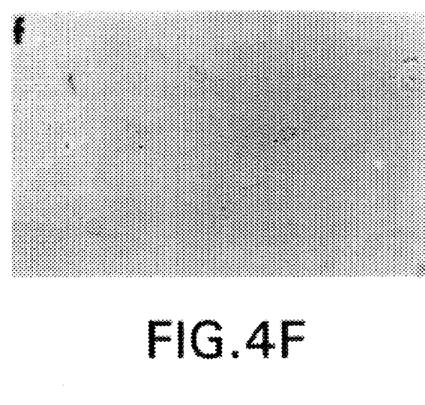

ST30 taken up by cells in vivo can act as a primer for the reverse transcription reaction in situ (FIG. 4A). Cytoplasmic signal was reproducibly observed when cells were incubated with S-oligo dT for 2 hours in vivo, and then Triton extracted, fixed and subjected to IST. Signal resulting from elongation of the transcripts was detected primarily in the perinuclear region of the cytoplasm, with about 30% of cells also showing nuclear signal. This intracellular distribution was similar to the pattern of transcripts detected when the primer was added after, instead of before, cell fixation (FIG. 4C). Controls showed that no reverse transcription was seen in the absence of primer (FIG. 4F), or in the presence of primer when RT was heat inactivated before IST (FIG. 4E). Similarly, use of S-oligo dA (SA30) as a primer, either before (FIG. 4B) or after fixation (FIG. 4D), did not result in signal. These experiments indicated that ST30 formed hybrids with cellular poly (A) RNA in vivo and that these hybrids could be detected specifically by exploiting their ability to prime synthesis of labeled transcripts by RT in situ.

Substantial silver stain was also observed when the above experiments were repeated using labeled dCTP, rather than dUTP, as substrate for IST, indicating that RT could copy mRNA sequences (containing G residues) upstream of the poly A tail. The intracellular distribution of silver stain was similar to the perinuclear distribution of hybridization signal observed using digoxigenin dUTP as label (FIG. 4A). Thus, antisense oligos added to cells in vivo prime reverse transcription in situ.

Figure 5A:
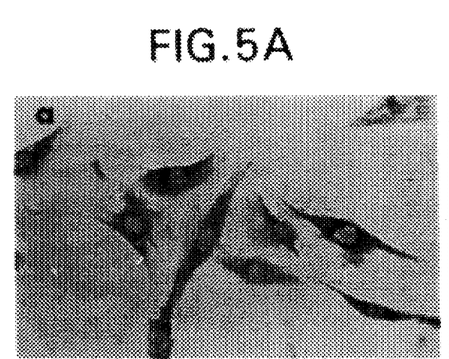
Figure 5B:
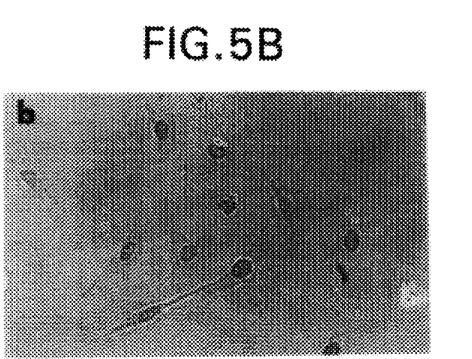
Figure 5C:
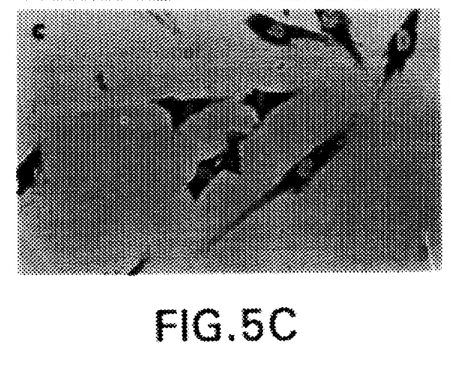
Figure 5D:
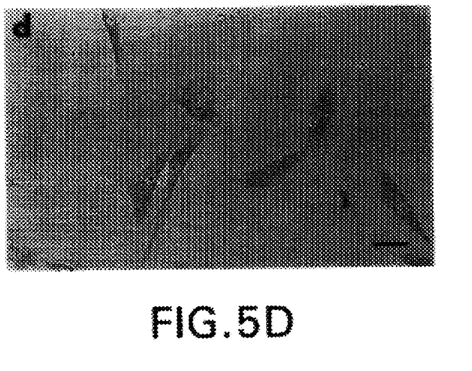

Other variously modified poly dT oligos were tested for their ability to act as primers for IST after their uptake by cells in vivo. Fluorescent derivatives of both S-oligo and O-oligo dTs (directly conjugated to either Texas red or FITC at positions internal to the 3' and 5' ends) were as effective as ST30 at priming the reverse transcriptase. FIG. 5A shows representative signal detected after treating cells with T43tr, a Texas Red labeled O-oligo, and detecting hybridization using the modified IST technique. ST30tr, the Texas red labeled analogue of ST30, also supports a high level of reverse transcription (FIG. 5C). The intracellular distribution of signal obtained after using the fluorescently labeled O-oligo or S-oligo appeared similar to the pattern seen after cells were treated with unlabeled ST30 (see FIG. 4A). Cells treated with the oligo dA analogues of these probes showed very low signal after IST (FIGS. 5B and 5D). Thus, fluorescently-labeled phosphodiester poly dT oligos also hybridize to intracellular RNA in vivo.

Hybridization can be detected in unextracted cells. As has been reported previously for IST (Bassell, G. J. et al., *J. Cell. Biol.* 126: 863–876 (1994)), signal from the modified IST performed here was highest when cells were permeabilized by Triton extraction and then fixed in paraformaldehyde/ glutaraldehyde. The majority of poly (A) RNA is strongly associated with the cytoskeleton and is detected in the Triton insoluble fraction of the cell using IST or in situ hybridization (ISH) techniques (Bassell, G. J. et al., *J. Cell. Biol.* 126: 863–876 (1994); Taneja, K. L. et al., *J. Cell. Biol.* 119: 1245–1260 (1992)). IST or ISH detection of poly (A) RNA gives similar patterns in extracted and unextracted cells (Bassell, G. J. et al., *J. Cell. Biol.* 126: 863–876 (1994); Taneja, K. L. et al., *J. Cell. Biol.* 119: 1245–1260 (1992)). Likewise, priming of the RT reaction was also detected after in vivo hybridization in unextracted cells, although the signal was sometimes less intense. Silver stained cells exhibit an intracellular distribution of signal that correlates with the perinuclear distribution pattern observed in cells that were Triton extracted before fixation (i.e., FIG. 4A). Thus, Triton extraction did not alter the distribution of poly (A) RNA in a way that affects the oligo hybridization pattern when compared to unextracted cells.

Figure 6A:
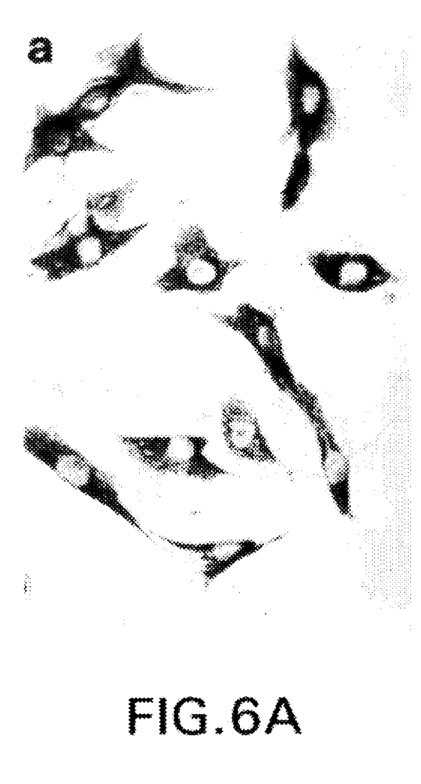
Figure 6B:
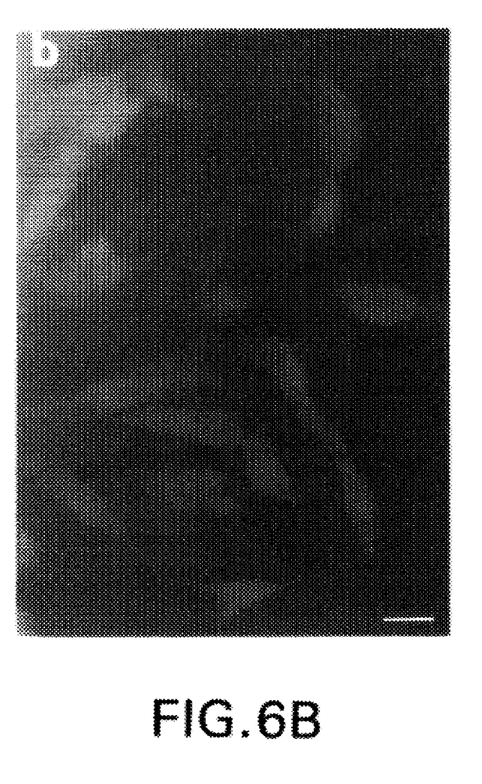

Because these cells were not fixed with glutaraldehyde, which induces autofluorescence, visualization of the fluorescent signal from ST30tr was possible in this same population of cells. This signal represented the cellular distribution of total ST30tr, both hybridized and unhybridized. In general, cytoplasmic fluorescent signal overlaps with the perinuclear location of silver stain. Less fluorescent signal or silver stain is seen in the extreme periphery of the cells. However, some cells and/or nuclei that contained oligo (as detected by fluorescence) did not show hybridization (silver stain) at all (compare two unlabeled cells in the middle of FIG. 6A to the fluorescent pattern in FIG. 6B). A simple explanation for this may be that the IST reagents cannot diffuse into unextracted cells or nuclei as readily as cells permeabilized by Triton extraction (see also Bassell, G. J. et al., *J. Cell. Biol.* 126: 863–876 (1994)).

To further substantiate IST detection of hybridization in vivo, intracellular hybridization was also measured using an alternate method. It was hypothesized that intracellular poly (A) that was part of a oligo/RNA hybrid would be unavailable for subsequent hybridization to an oligo dT probe after fixation of the cell and in situ hybridization.

Cells were incubated with ST30tr for 2 hours, fixed in 4% formaldehyde and then hybridized to a FITC labeled oligo dT probe (T43f) in situ. The amount of FITC fluorescence per cell was reduced to an average of 33.4% (n=227, s.e.=0.85%) when compared to untreated cells hybridized to T43f in situ. In contrast, cells treated with poly dA (SA30tr) in vivo did not show a decrease in the amount of T43f hybridized in situ, and in fact, some increase was seen, probably due to the internalized poly dA oligo providing additional targets. These results substantiate the IST findings and show that hybridization of ST30tr to poly (A) RNA in vivo reduces the number of targets available for hybridization to a similar probe in situ. Thus, uptake of oligo dT in vivo inhibits subsequent in situ hybridization.

EXAMPLE 10

Kinetics of Hybridization In Vivo

Figure 7A:
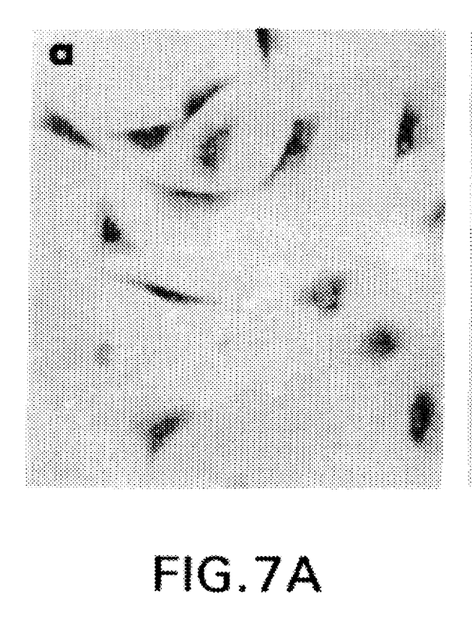
FIGS. 7A–7B are photomicrographs showing in vivo hybridization as a function of external oligo concentration and incubation time. Cells were incubated with oligo for varying times or at varying concentrations of oligo, extracted, fixed and subjected to IST. Silver stain was quantitated after cells were imaged (FIG. 7A; T43tr) and cells segmented from background (FIG. 7B in black outlines) using an automated image analysis system. Bright field images, bar=20 microns.
Figure 7B:
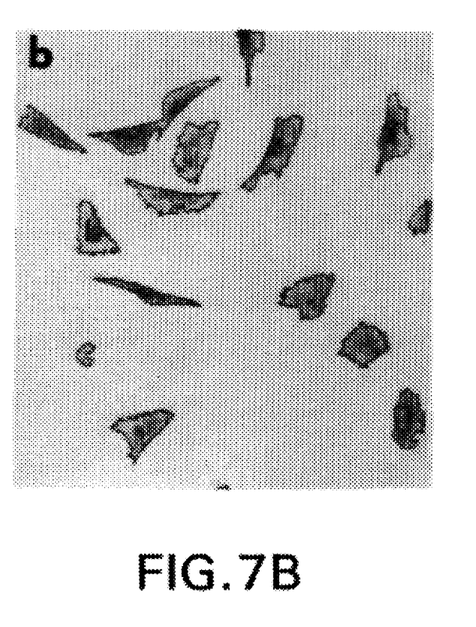
Figure 7C:
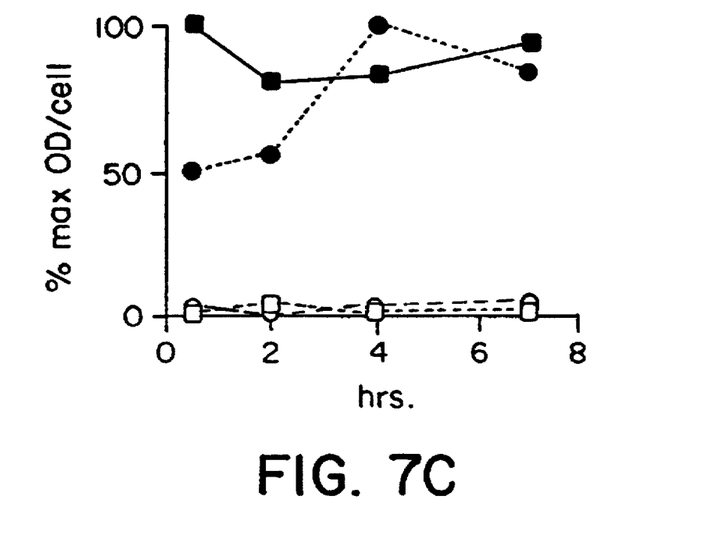
FIG. 7C is a graphical representation showing in vivo hybridization of the probes ST30tr (-■-) and T43tr (-●-) and their dA analogues (-□- and -○-) as a function of incubation time.
Figure 7D:
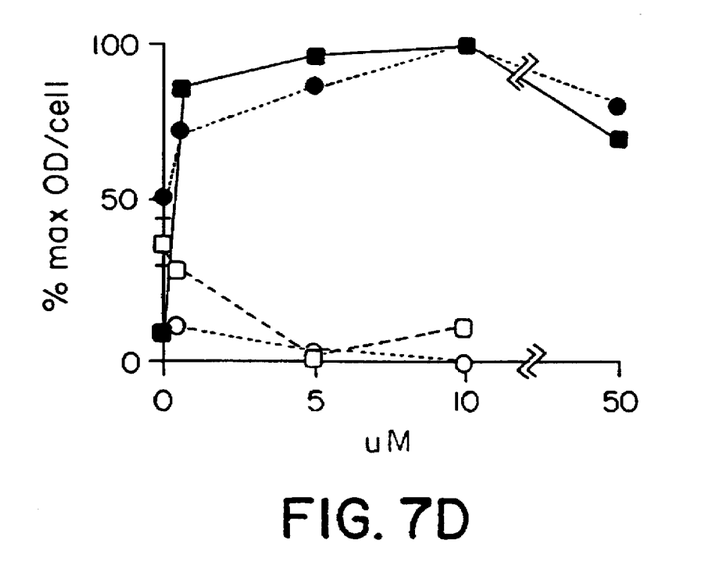
FIG. 7D is a graphical representation showing in vivo hybridization of the probes ST30tr (-■-) and T43tr (-●-) and their dA analogues (-□- and -○-) as a function of external probe concentration.

Using the modified IST technique described herein, the amount of oligo dT hybridization to poly A RNA in live cells was quantitated as a function of both incubation time and oligo concentration during uptake. Living cells were exposed to varying amounts of fluorescent S-oligo or O-oligo dT for varying amounts of time and then extracted and fixed. IST was performed with silver enhanced signal detection as described above and average silver stain present per cell was quantitated using an automated digital image analysis system sold under the trademark "DISCOVERY" (Becton Dickinson Cellular Imaging Systems, San Jose, Calif.) (FIGS. 7A–7B). FIG. 7C shows that intracellular hybridization was reproducibly detected after cells had been incubated with ST30tr for 30 minutes. Signal resulting from hybridization was detected as early as 5 minutes after ST30tr oligo treatment began. Similar kinetics were observed when O-oligo dT was used, although saturation was not reached as early. These results correlated with intracellular quantitation of fluorescence. Oligo that entered the cell rapidly (as measured by fluorochrome detection) also hybridized rapidly (represented by silver stain). FIG. 7D shows that the maximal detectable hybridization in the cell occurs at external oligo concentrations of about 0.5 µM for both T43tr and ST30tr. Therefore, hybridization appears to saturate at lower concentrations than those required for internalized S-oligo to reach a steady state (concentration greater than 1 µM). The intracellular distribution of hybridization does not change at the light microscopy level as the concentration or time of incubation increases.

FIGS. 7C and 7D show in vivo hybridization as a function of external oligo concentration and incubation time. Cells were incubated with oligo for varying times or at varying concentrations of oligo, extracted, fixed and subjected to IST. Silver stain was quantitated after cells were imaged and cells segmented from background using an automated image analysis system sold under the trademark "DISCOVERY" (Becton Dickinson Cellular Imaging Systems, San Jose, Calif.). FIG. 7C is a plot showing silver stain absorbance/ cell after treatment with 0.1 µM ST30tr (-■-) or T43tr (-●-) and their dA analogues (-□- and -○-), respectively, for various times. FIG. 7D is a plot showing silver stain absorbance/cell after treatment with ST30tr (-■-) or T43tr (-●-) and their dA analogues (-□- and -○-), respectively, at various concentrations after incubation for about 2 hours.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for detecting target nucleic acids in a living cell or tissue, comprising the steps of:
   a) incubating the living cell or tissue with a labelled single-stranded oligonucleotide probe under conditions suitable for uptake of said probe and its specific hybridization to complementary nucleic acids in the cell or tissue, said oligonucleotide having a nucleotide sequence complementary to the target nucleic acids;
   b) washing the cell or tissue to allow unhybridized probe to exit from the cell or tissue; and
   c) detecting presence of the labelled probe in the cell or tissue after step b) is performed, wherein detection of the labelled probe in the cell or tissue indicates the presence of the target nucleic acids in the cell or tissue.

2. The method of claim 1, wherein the oligonucleotide is unmodified.

3. The method of claim 1, wherein the oligonucleotide is modified to increase its ability to penetrate cellular membranes, thereby producing a modified single-stranded oligonucleotide probe.

4. The method of claim 3, wherein the oligonucleotide has at least one substitution of a phosphate backbone oxygen that decreases the hydrophilicity of the modified oligonucleotide compared to an unmodified oligonucleotide.

5. The method of claim 4, wherein the modification of the oligonucleotide is selected from the group consisting of:
   a) phosphorothioate; and
   b) phosphorodithioate.

6. The method of claim 3, wherein the probe is an oligonucleotide with a 3'-end blocking group.

7. The method of claim 6, wherein the 3'-end blocking group is selected from the group consisting of:
   a) amino-modified nucleotide;
   b) methyl group;
   c) fluorochrome-conjugated group;
   d) 3' to 5' nucleotide linkage; and
   e) succinyl ester group.

8. The method of claim 1, wherein the probe is labelled with a fluorochrome.

9. The method of claim 1, wherein in step a), two or more differently labelled probes are used, and wherein each said probe has a nucleotide sequence complementary to different target nucleic acids.

10. The method of claim 3, wherein in step a), the cell or tissue is incubated with a labelled probe and an unlabelled oligonucleotide with a nucleotide sequence different from the nucleotide sequence of the labelled probe, wherein the unlabelled oligonucleotide has the same modification as the labelled oligonucleotide.

11. The method of claim 1, wherein in step b), the cell or tissue is washed in medium containing unlabelled probe which has a nucleotide sequence that is not complementary to the target nucleic acids.

12. The method of claim 1, wherein the target nucleic acid are RNAs.

13. The method of claim 1, wherein the target nucleic acids are from an infectious agent.

14. The method of claim 13, wherein the infectious agent is a virus.

15. The method of claim 1, wherein the target nucleic acids are antisense oligonucleotides.

16. The method of claim 1, wherein in step c), detecting presence of the labelled probe in the cell or tissue comprises a method selected from the group consisting of:
   a) fluorescence microscopy;
   b) flow cytometry; and
   c) image analysis.

17. The method of claim 1, wherein in step c), detecting presence of the labelled probe in the cell or tissue comprises quantitating the amount of labelled probe detected, wherein the amount of labelled probe detected indicates the amount of the target nucleic acids in the cell or tissue.

18. A method for detecting target nucleic acids in a living cell or tissue, comprising the steps of:
   a) incubating the cell or tissue in a physiologically acceptable medium in which cells are able to grow and/or divide and containing a fluorochrome-labelled, single-stranded oligonucleotide probe, under conditions suitable for uptake of said probe and its specific hybridization to complementary nucleic acids in the cell or tissue, said oligonucleotide having a nucleotide sequence complementary to the target nucleic acids;
   b) removing the medium containing the probe and washing the cell or tissue in medium without probe; and
   c) detecting fluorescence of the probe in the cell or tissue after step b) is performed, wherein fluorescence indicates the presence of the target nucleic acids in the cell or tissue.

19. A method for detecting target nucleic acids in a living cell or tissue, comprising the steps of:
   a) incubating the living cell or tissue with a single-stranded oligonucleotide probe under conditions suitable for uptake of said probe and its specific hybridization to complementary nucleic acids in the cell or tissue, said oligonucleotide having a nucleotide sequence complementary to the target nucleic acids and modified to increase its ability to penetrate cellular membranes, wherein said probe is hydrolyzed by nucleases when not hybridized and is not hydrolyzed by nucleases when hybridized to complementary nucleic acids; and
   b) detecting presence of the probe in the cell or tissue, wherein detection of the probe in the cell or tissue indicates the presence of the target nucleic acids in the cell or tissue.

20. A method for detecting target nucleic acids in a living cell or tissue, comprising the steps of:
   a) incubating the living cell or tissue with probes comprising a first and a second single-stranded oligonucleotide under conditions suitable for uptake of said probes and their specific hybridization to complementary nucleic acids in the cell or tissue, wherein the first and the second oligonucleotides are complementary to immediately adjacent sites on the target nucleic acid sequence, the first oligonucleotide with its 5' end closest to the 3' end of the second oligonucleotide when hybridized to immediately adjacent sites on the target nucleic acid sequence being labelled on the 5' end with either an energy donor group or an energy acceptor group and the second oligonucleotide being labelled on the 3' end with whichever group, either an energy donor group or an energy acceptor group, not being used as a label on the first oligonucleotide;
   b) washing the cell or tissue to allow unhybridized probe to exit from the cell or tissue; and
   c) detecting energy transfer between the first and the second oligonucleotides after step b) is performed, wherein energy transfer indicates the presence of the target nucleic acids in the cell or tissue.

21. A method for detecting expression of target nucleic acids in a living cell or tissue, comprising the steps of:
   a) incubating the living cell or tissue with a labelled single-stranded oligonucleotide probe under conditions suitable for uptake of said probe and its specific hybridization to complementary RNA nucleotides in the cell or tissue, said oligonucleotide having a nucleotide sequence complementary to the target nucleic acids;
   b) washing the cell or tissue to allow unhybridized probe to exit from the cell or tissue; and
   c) detecting presence of the labelled probe in the cell or tissue after step b) is performed, wherein detection of the labelled probe in the cell or tissue indicates that the cell or tissue expresses the target nucleic acids.

22. The method of claim 21, wherein in step c), detecting presence of the labelled probe in the cell or tissue comprises quantitating the amount of labelled probe detected, wherein the amount of labelled probe detected indicates the level of expression of the target nucleic acids in the cell or tissue.

23. A method for monitoring the expression of target nucleic acids in a living cell or tissue comprising performing the method of claim 21 on the same cell or tissue sample more than once.

24. A method for identifying a cell that expresses target nucleic acids, comprising the steps of:

a) incubating a population of living cells with a labelled single-stranded oligonucleotide probe under conditions suitable for uptake of said probe and its specific hybridization to complementary RNA nucleotides in the cells, said oligonucleotide having a nucleotide sequence which is complementary to the target nucleic acids;

b) washing the cells to allow unhybridized probe to exit from the cell; and c) detecting presence of the labelled probe in the cell after step b) is performed, wherein detection of the labelled probe in the cell indicates that the cell expresses the target nucleic acids.

25. The method of claim 24, further comprising separating the expressing cell from nonexpressing cells in the cell population.

26. The method of claim 25, wherein the separating step comprises a method selected from the group consisting of:

a) flow sorting; and b) microdissection followed by subcloning of microdissected cells.

27. A method for locating target nucleic acids in a living cell or tissue, comprising the steps of:

a) incubating the living cell or tissue with a single-stranded oligonucleotide probe under conditions suitable for uptake of said probe and its specific hybridization to complementary nucleic acids in the cell or tissue, said oligonucleotide having a nucleotide sequence which is complementary to the target nucleic acids;

b) washing the cell or tissue to allow unhybridized probe to exit from the cell or tissue; and c) detecting presence of the probe in the cell or tissue after step b) is performed, wherein detection of the probe in the cell or tissue indicates the location of the target nucleic acids in the cell or tissue.

28. A method for confirming hybridization of an oligonucleotide probe to its complementary target nucleic acids in a cell or tissue, comprising the steps of:

a) incubating the living cell or tissue with a single-stranded oligonucleotide probe under conditions suitable for uptake of said probe and its specific hybridization to complementary nucleic acids in the cell or tissue, said oligonucleotide having a nucleotide sequence complementary to the target nucleic acids;

b) washing the cell or tissue to allow unhybridized probe to exit from the cell or tissue, thereby obtaining a washed cell or tissue;

c) fixing the washed cell or tissue; and d) detecting presence of the probe in the cell or tissue by in situ transcription after step c) is performed, wherein a signal generated by in situ transcription indicates hybridization of the probe to its complementary target nucleic acids in the cell or tissue.

* * * * *